United States Patent
Palaniappan et al.

(10) Patent No.: US 6,743,942 B1
(45) Date of Patent: Jun. 1, 2004

(54) PROCESS FOR THE TRANSESTERIFICATION OF KETO ESTER WITH ALCOHOL USING POLYANILINE SALTS AS CATALYST

(75) Inventors: Srinivasan Palaniappan, Hyderabad (IN); Rampally Chandrashekhar, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/290,475

(22) Filed: Nov. 8, 2002

(51) Int. Cl.$^7$ .......................... C07C 69/66; C07C 69/72
(52) U.S. Cl. .................. 560/145; 560/174; 560/178
(58) Field of Search .................. 560/174, 145, 560/178

(56) References Cited

U.S. PATENT DOCUMENTS 6,376,701 B1    4/2002  Chavan et al.

OTHER PUBLICATIONS

S. Palaniappan et al, "Esterification of carboxylic acids with alcohols catalyzed by polyaniline salts" Green Chemistry, vol. 4(1), pp. 53–55 (2002).*

Prabhakaran and Iqbal, "Polyaniline–Supported Cobalt Catalyst: A Three–Component Condensation Route to beta–Amino Acid Derivatives" Journal of Organic Chemistry, vol. 64, pp. 3339–3341 (1999).*

Kirk–Othmer Encyclopedia of Chemical Technology (Ed., Jacqueline I. Kroschwitz), 4$^{th}$ Edition, vol. 9, pp. 774–780.

C. Holmquist et al., "A Selective Method for the Direct Conversion of Aldehydes into β–Keto Esters with Ethyl Diazoacetate Catalyzed by Tin(II) Chloride," *J. Org. Chem.* 1989, pp. 3258–3260, American Chemical Society.

D. Taber et al., "Preparation of β–Keto Esters by 4–DMAP-Catalyzed Ester Exchange," *J. Org. Chem.*, 1985, pp. 3618–3619, American Chemical Society.

B. Kumar et al., "Iron (III) perchlorate: A reagent for trans–esterification," *Indian Journal of Chemistry*, Feb. 1993, vol. 32B:292–293.

B. Balaji et al., "Simple and High Yielding Syntheses of β–Keto esters Catalysed by Zeolites," *Tetrahedron*, 1998, vol. 54:13237–13252, Elsevier Science Ltd.

J. Otera et al., "Novel Template Effects of Distannoxane Catalysts in Highly Efficient Transesterification and Esterification," *J. Org. Chem.*, 1991, 56(18):5307–5311, American Chemical Society.

D. Ponde et al., "Selective Catalytic Transesterfication, Transthiolesterification, and Protection of Carbonyl Compounds over Natural Kaolinitic Clay," *J. Org. Chem.* 1998, 63:1058–1063, American Chemical Society.

S. Chavan et al., "Transesterification of Ketoesters Using Amberlyst–15," *Synthetic Communications*, 2001, 31(2):289–294, Marcel Dekker, Inc.

B. Bandgar et al., "Sodium Perborate Catalyzed Selective Transesterification of β–Keto Esters Under Neutral Conditions," *Chemistry Letters 2001*, pp. 894–895, The Chemical Society of Japan.

S. Palaniappan et al., "Composition and Spectral Studies of Polyaniline Salts," *Polymers for Advanced Technologies*, 5:225–230, John Wiley & Sons, Ltd.

S. Palaniappan et al., "Tetrahydropyranylation of alcohols catalyzed by polyaniline salts," *Green Chemistry*, 2002, 4:369–371, The Royal Society of Chemistry.

B. Reddy et al., "Mo–ZrO$_2$ Solid Acid Catalyst for Transterification of β–Ketoesters," *Synthetic Communications* 1999, 29(7):1235–1239, Marcel Dekker, Inc.

* cited by examiner

*Primary Examiner*—Richard L. Raymond
*Assistant Examiner*—Zachary C. Tucker
(74) *Attorney, Agent, or Firm*—Foley & Lardner LLP

(57) ABSTRACT

The present invention provides a process for transesterification of ketoester using polyaniline salt as catalyst, said process comprising reacting a keto ester with an alcohol in presence of a catalyst at a temperature range of 50 to 120° C. for a period in the range of 4 to 24 hours and separating the esters from the reaction mixture.

9 Claims, No Drawings

PROCESS FOR THE TRANSESTERIFICATION OF KETO ESTER WITH ALCOHOL USING POLYANILINE SALTS AS CATALYST

FIELD OF THE INVENTION

The present invention relates to a process for the transesterification of keto esters with alcohols using polyaniline salts as catalyst.

BACKGROUND AND PRIOR ART REFERENCES

Transesterification is a reaction between an ester and other compound, characterized by an exchange of alkoxy groups or of acyl groups and resulting in the formation of a different ester. Three types of transesterification are known (Kirk-Othmer Encyclopedia of Chemical Technology (Ed., Jacqueline I. Kroschwitz), 4$^{th}$ Edition, Vol.9, Page 774 and references therein)

1. Exchange of alcohol groups, commonly known as alcoholysis. In this process the compound with which an ester reacts is an alcohol.

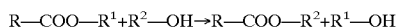
R—COO—R$^1$+R$^2$—OH→R—COO—R$^2$+R$^1$—OH

2. Exchange of acid groups, acidolysis. In this process the compound with which an ester reacts is an acid

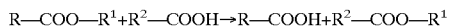
R—COO—R$^1$+R$^2$—COOH→R—COOH+R$^2$—COO—R$^1$ 3. ester—ester interchange. In this process an exchange takes place between two esters

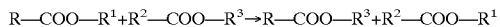
R—COO—R$^1$+R$^2$—COO—R$^3$→R—COO—R$^3$+R$^2$—COO—R$^1$

A normal method of transesterification is characterized by equilibrium between reactants and products. Generally, one of the reactants should be added in excess to move the reaction towards forward direction and obtain good yields.

Transesterification is more advantageous than the ester synthesis from carboxylic acid and alcohol, due to poor solubility of some acids in organic solvents. Some esters, especially methyl and ethyl esters, are readily or commercially available and thus serve conveniently as starting materials in transesterification.

Transesterification via alcoholysis plays a significant role in industry as well as in laboratory and in analytical chemistry. The reaction can be used to reduce the boiling point of esters by exchanging a long chain alcohol group with a short one e.g. methanol, in the analysis of fats, oils and waxes. Transesterification is applicable in the paint industry for curing alkyl resin. It plays an important role in polymerization and in cosynthesis of ethylene glycol and dimethyl carbonate from ethylene carbonate and methanol.

β-Ketoesters represents an important class of organic building blocks and is used for efficient synthesis of a number of complex natural products. β-Ketoesters are multicoupling reagents with electrophilic and nucleophilic sites proven to be valuable tools in a wide variety of molecular systems. These β-ketoesters are important by virtue of their facile bond formation at all four carbon atoms that feature in their ease of transformation to chiral building blocks and use in chain extension reactions. They are one of the basic building blocks in the total synthesis of sex pheromones like serricornine and other natural products like thiolactomycin, trichodiene, polyoximic acid, chokol, protaglandin PGF$_{2\alpha}$, ar-pseudotsugonoxide, syncarpic acid, diplodialide and podophyllotoxin.

Most of the methods of transesterification of ketoesters are not general and are equilibrium driven reactions where usage of excess of one of the reactants is mandatory to obtain good yields. Process for transesterification of keto esters has been carried out by using various catalysts such as Lewis acids (Holmquist et al. J Org Chem., 1989; 54:3258), Dimethylamino pyridine (Taber et al. J. Org. Chem., 1985; 50: 3618), Iron (III) perchlorate (Kumar et al. Ind. J. Chem., 1993; 32B: 292), Zeolites (Balaji et al. Tetrahedron 1998; 54: 13237), Distannoxane (Otera et al. J. Org. Chem. 1991; 56 (18):5307), Natural kaolinitic clay (Ponde et al. J. Org. Chem. 1998; 63: 1058), Amberlyst-15 (Chavan et al. Synth. Commun. 2001; 31(2): 289), Mo—ZrO$_2$ solid acid (Reddy et al. Synth. Commun. 1999; 29 (7): 1235), Sodium perborate (Bandagar et al; Chemistry Letters, 2001; 894), Solid acid catalyst (Chavan et al. U.S. Pat. No. 6,376,701, 2002).

Esterification is one of the most fundamental and important reactions in organic synthesis. Conventionally, the processes of making esters can be classified into the following three main categories:

(a) Liquid-phase esterification reaction utilizing a liquid catalyst: This type of processes utilize liquid phase acid, such as sulfuric acid, phosphoric acid, or sulfonic acid, as catalysts.

(b) Liquid phase esterification reaction utilizing a solid catalyst: This type of processes typically utilizes inorganic salts, cationic ion exchange resin and solid acid catalyst etc.

(c) Gas phase esterification reaction: This type of processes utilize a variety of catalysts such as heteropolyacids, liquid phase acids carried by a solid carrier, and zeolite in a gas phase reaction.

One of the problems associated with the liquid-phase esterification reaction using liquid-catalyst is that the acidic catalysts of sulfuric acid or sulfonic acid can cause corrosion problems to the reactor. These liquid acid catalysts are also discharged along with the reaction products, thus causing severe waste disposal and pollution problems. The drawbacks of using mineral acid as catalyst are: (i)Catalyst can not be reused, (ii) Disposal of acid is not environmentally safe and it is not economical, (iii) Low selectivity is frequently observed, (iv) Corrosion of the reaction vessel and reactors, (v) Not easy to handle and (vi) High inventory of the catalyst.

The solid-catalyst liquid-phase esterification reaction, which typically utilizes a cationic ion exchange resin as catalyst, ameliorates the corrosion and waste disposal problems experienced with the liquid-catalyst liquid-phase processes, and results in simplified separation procedure required between the reaction product and catalysts. However, cationic ion-exchange resins typically exhibit relatively poor heat-resistance, and they often lose substantial activity after being subject to heat. Once the catalytic activity of the cationic ion-exchange resins is reduced, it is difficult to be regenerated.

In the gas phase esterification reaction, the reaction conditions are maintained so that all the reactants and products are in the gas phase. Typically, inorganic materials are utilized as catalysts which typically exhibit excellent heat resistance and can be easily separated from the reaction products. However, the gas phase reaction necessitates a relatively large reaction vessel, resulting in large capital investment cost. Furthermore, if the gas phase esterification reaction is utilized to produce unsaturated carboxylic esters, the high reaction temperature often causes undesired by-products of polymers or oligomers to be produced. In certain instances, the high reaction temperature has caused the alcohol molecules to be dehydrated to become ethers. These side-reactions will tend to cause the reaction catalysts to lose their activity and result in operational difficulties.

OBJECTS OF THE INVENTION

The main object of the present invention is to provide a process for the transesterification of keto esters with alcohols using polyaniline salts as catalysts, which obviates the drawbacks as detailed above.

Another object of the invention is to provide an eco-friendly process for the transesterfication of ketoester.

SUMMARY OF THE INVENTION

Accordingly, the present invention provides a process for transesterification of ketoester using polyaniline salt as catalyst by reacting said keto ester with an alcohol in presence of a catalyst and separating the esters from the reaction mixture.

DETAILED DESCRIPTION OF THE INVENTION

Accordingly, the present invention provides a process for transesterification of ketoester using polyaniline salt as catalyst, said process comprising reacting a keto ester with an alcohol in presence of a catalyst at a temperature range of 50 to 120° C. for a period in the range of 4 to 24 hours and separating the esters from the reaction mixture.

One embodiment of the invention relates to a process, in which the alcohol used is selected from a group consisting of butanol, hexanol, octanol, decanol, dodecanol, behnyl alcohol, benzyl alcohol, cyclohexanol, 2-ethoxy ethanol, 2-butoxy ethanol, 3-butyne-1-ol, allyl alcohol, and menthol.

Another embodiment of the invention, the catalyst used is a polyaniline salt selected from a group consisting of polyaniline-sulfuric acid, polyaniline-hydrochloric acid and polyaniline-nitric acid system.

Still another embodiment, the preferred reaction temperature is in the range of 100 to 110° C.

Still another embodiment, the ketoester used is selected from a group consisting of methyl acetoacetate, ethyl acetoacetate and phenyl acetoacetate.

Yet another embodiment, the reaction is carried out for a period of 20 to 24 hours.

Yet another embodiment, the catalyst amount used is in the range of 10 to 30 weight percent of ketoester Still yet another embodiment provides a process, wherein the amount of alcohol used is 1.0 to 2.5 equivalent with respect to one equivalent of keto ester.

Another embodiment of the invention, the catalyst used is recycled.

These embodiments will be apparent from the ensuing detailed description of the present invention.

The process of transesterification may be carried out by reacting keto ester with alcohol in presence of catalyst, and then removing the catalyst by conventional methods. The ester can be isolated by methods such as filtration followed by isolation of esters by conventional column chromatography or vacuum distillation.

The novelty of the invention lies in the use of polyaniline-salts as catalysts in the liquid phase esterification of keto esters with alcohols for the first time. Also, the use of polyaniline salts as catalysts provides the following advantages (i) separation of catalyst from a reaction mixture is easy, (ii) repeated use of catalyst is possible and (iii) there is no problem for the disposal of used catalyst as they are environmentally safe.

The following examples are given by way of illustration and therefore should not be construed as limit the scope of the present invention.

EXAMPLE 1

The following example illustrates the preparation of esters with different reaction time.

In a typical experiment, one equivalent (1.0 g) of ethyl acetoacetate was taken in 10 ml round bottom flask and added two equivalent (1.5 g) of hexanol followed by 200 mg of polyaniline-sulfate salt catalyst powder (20 wt % with respect to ethyl acetoacetate). The reaction mixture was refluxed at 110° C. for different intervals of time. The reaction mixture was filtered, washed with dichloromethane solvent and the solvent was evaporated. The percentage conversion of ethyl acetoacetate was estimated by $^1$H NMR spectra using Varian Gemini 200 MHz spectrometer.

The percentage conversion of ethyl acetoacetate with different reaction time is given in Table 1.

TABLE 1

| REACTION TIME (hrs.) | CONVERSION (%) |
| --- | --- |
| 4 | 42 |
| 8 | 76 |
| 10 | 84 |
| 14 | 87 |
| 16 | 96 |
| 20 | 96 |
| 24 | 96 |

EXAMPLE 2

The following example illustrates the preparation of esters with different amount of catalyst.

In a typical experiment, one equivalent (1.0 g) of ethyl acetoacetate was taken in 10 ml round bottom flask and added two equivalent (1.5 g) of hexanol followed by different amount of catalyst powder (polyaniline-sulfate salt). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl acetoacetate with different amount of catalyst is given in Table 2.

TABLE 2

| AMOUNT OF CATALYST (mg.) | CONVERSION (%) |
| --- | --- |
| 100 | 92 |
| 150 | 96 |
| 200 | 96 |
| 300 | 96 |

EXAMPLE 3

The following example illustrates the preparation of esters with different amount of alcohol.

In a typical experiment, one equivalent (1.0 g) of ethyl acetoacetate was taken in 10 ml round bottom flask and added different equivalent of hexanol followed by 200 mg of polyaniline-sulfate salt catalyst powder (20 wt % with respect to ethyl acetoacetate). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl acetoacetate with different amount of alcohol is given in Table 3.

TABLE 3

| Ethylacetoacetate:Hexanol (equivalent) | CONVERSION (%) |
|---|---|
| 1.0:1.0 | 67 |
| 1.0:1.2 | 77 |
| 1.0:1.5 | 90 |
| 1.0:2.0 | 96 |

EXAMPLE 4

The following example illustrates the preparation of esters with different temperature.

In a typical experiment, one equivalent (1.0 g) of ethyl aceto acetate was taken in 10 ml round bottom flask and added two equivalent (1.5 g) of hexanol and 200 mg of catalyst powder (polyaniline-sulfate salt). The reaction mixture was refluxed at different temperatures for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl acetoacetate with different temperature is given in Table 4.

TABLE 4

| TEMPERATURE (° C.) | CONVERSION % |
|---|---|
| 90 | 51 |
| 110 | 96 |
| 120 | 85 |

EXAMPLE 5

The following example illustrates the preparation of esters with different alcohol.

In a typical experiment, one equivalent (1.0 g) of ethyl acetoacetate was taken in 10 ml round bottom flask and added two equivalent of different alcohol and 200 mg of catalyst powder (polyaniline-sulfate salt). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl acetoacetate with different alcohol is given in Table 5.

TABLE 5

| ALCOHOL | CONVERSION (%) |
|---|---|
| Butanol | 94 |
| Hexanol | 96 |
| Octanol | 94 |
| Decanol | 90 |

TABLE 5-continued

| ALCOHOL | CONVERSION (%) |
|---|---|
| Dodecanol | 92 |
| Behnyl alcohol | 94 |
| Benzyl alcohol | 72 |
| Cyclohexanol | 85 |
| 2-ethoxy ethanol | 96 |
| 2-butoxy ethanol | 96 |
| 3-butyne-1-ol | 90 |
| Allyl alcohol | 23 |
| Menthol | 94 |

EXAMPLE 6

The following example illustrates the preparation of esters with different keto ester.

In a typical experiment, one equivalent (1.0 g) of keto ester was taken in 10 ml round bottom flask and added two equivalent (1.5 g) of hexanol and 200 mg of catalyst powder (polyaniline-sulfate salt). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl acetoacetate with different keto ester is given in Table 6.

TABLE 6

| KETO ESTER | CONVERSION (%) |
|---|---|
| Methyl acetoacetate | 96 |
| Ethyl acetoacetate | 96 |
| Phenyl acetoacetate | 90 |

EXAMPLE 7

The following example illustrates the preparation of esters using the recovered catalyst for three times.

In a typical experiment, one equivalent (1.0 g) of ethyl acetoacetate was taken in 10 ml round bottom flask and added two equivalent of decanol followed by 200 mg of polyaniline-sulfate salt catalyst powder (20 wt % with respect to ethyl acetoacetate). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The experiment was carried out three times more using the recovered catalyst. The yield of the ester prepared with recovered catalyst is given in Table 8.

TABLE 8

| REPEATABILITY (no of times) | CONVERSION (%) |
|---|---|
| First | 90 |
| Second | 88 |
| Third | 90 |

EXAMPLE 9

The following examples illustrate the preparation of esters with different catalyst.

Polyaniline salts were prepared using ammonium persulfate oxidizing agent (Method I, See Palaniappan et al. Poly.

Adv. Tech., 1994, 5: 225 ) and benzoyl peroxide oxidizing agent (Method II, See Palaniappan et al. Green Chemistry, 2002; 4: 369).

In a typical experiment, one equivalent (1.0 g) of ethyl acetoacetate was taken in 10 ml round bottom flask and added two equivalent (1.5 g) of hexanol followed by 200 mg of different polyaniline salt (polyaniline-hydrochloride, polyaniline-sulfate, polyaniline-nitrate salt) catalyst powder (20 wt % with respect to ethyl acetoacetate). The reaction mixture was refluxed at 110° C. for 24 hrs. The reaction mixture was filtered, washed with dichloromethane solvent and the solvent was evaporated. The percentage conversion of ethyl acetoacetate was estimated by $^1$H NMR spectra.

The percentage conversion of ethyl aceto acetate with different catalyst is given in Table 9.

TABLE 9

| METHOD | POLYANILINE SALT | CONVERSION (%) |
|---|---|---|
| I | Polyaniline hydrochloric acid system | 90 |
|  | Polyaniline sulfuric acid system | 96 |
|  | Polyaniline nitric acid system | 94 |
| II | Polyaniline hydrochloric acid system | 91 |
|  | Polyaniline sulfuric acid system | 96 |
|  | Polyaniline nitric acid system | 94 |

ADVANTAGES OF THE PRESENT INVENTION

The main advantages of the present invention are a) Use of polyaniline-salts as catalysts in the liquid phase esterification of keto esters with alcohols for the first time.

b) Also, the use of polyaniline salts as catalysts provides the following advantages
   (i) separation of catalyst from a reaction mixture is easy,
   (ii) repeated use of catalyst is possible,
   (iii) there is no problem for the disposal of used catalyst as they are environmentally safe, though the disposal of mineral acid catalyst requires much money for treatment to make it environmentally safe, and
   (iv) the preparation of the catalyst is straight forward synthetic route.

In view of the above, it can be seen that several advantages of the invention are achieved and other advantageous results attained. As various changes could be made in the above methods and compositions without departing from the scope of the invention, it is intended that all matter contained in the above description shall be interpreted as illustrative and not in a limiting sense.

What is claimed is:

1. A process for transesterification of ketoester using polyaniline salt as catalyst, said process comprising reacting a keto ester with an alcohol in presence of a catalyst at a temperature range of 50 to 120° C. for a period in the range of 4 to 24 hours and separating the esters from the reaction mixture.

2. A process as claimed in claim 1, wherein the alcohol used is selected from a group consisting of butanol, hexanol, octanol, decanol, dodecanol, behnyl alcohol, benzyl alcohol, cyclohexanol, 2-ethoxy ethanol, 2-butoxy ethanol, 3-butyne-1-ol, allyl alcohol, and menthol.

3. A process as claimed in claim 1, wherein the catalyst used is a polyaniline salt selected from a group consisting of polyaniline-sulfuric acid, polyaniline-hydrochloric acid and polyaniline-nitric acid system.

4. A process as claimed in claim 1, wherein the reaction is carried out preferably at a temperature range of 100 to 110° C.

5. A process as claimed in claim 1, wherein the ketoester used is selected from a group consisting of methyl acetoacetate, ethyl acetoacetate and phenyl acetoacetate.

6. A process as claimed in claim 1, wherein the reaction is carried out for a period of 20 to 24 hours.

7. A process as claimed in claim 1, wherein the catalyst amount used is in the range of 10 to 30 weight percent of ketoester.

8. A process as claimed in claim 1, wherein the amount of alcohol used is 1.0 to 2.5 equivalent with respect to one equivalent of keto ester.

9. A process as claimed in claim 1, wherein the catalyst used is recyclable.

* * * * *